United States Patent
Palepu et al.

(10) Patent No.: US 9,238,037 B2
(45) Date of Patent: *Jan. 19, 2016

(54) ENEMA COMPOSITION FOR TREATMENT OF ULCERATIVE COLITIS HAVING LONG TERM STABILITY

(71) Applicant: SciDose, LLC, Amherst, MA (US)

(72) Inventors: Nagesh R. Palepu, Southampton, PA (US); Philip Christopher Buxton, Great Dunmow (GB)

(73) Assignee: SciDose, LLC, Amherst, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/326,096

(22) Filed: Jul. 8, 2014

(65) Prior Publication Data

US 2014/0323449 A1    Oct. 30, 2014

Related U.S. Application Data

(63) Continuation of application No. 14/076,560, filed on Nov. 11, 2013, now Pat. No. 8,809,308.

(60) Provisional application No. 61/724,678, filed on Nov. 9, 2012.

(51) Int. Cl.
| | |
|---|---|
| *A61K 31/56* | (2006.01) |
| *A61K 31/58* | (2006.01) |
| *A61K 31/352* | (2006.01) |
| *A61K 9/00* | (2006.01) |
| *A61K 47/12* | (2006.01) |
| *A61K 9/08* | (2006.01) |
| *A61K 31/196* | (2006.01) |
| *A61K 31/353* | (2006.01) |

(52) U.S. Cl.
CPC ............... *A61K 31/58* (2013.01); *A61K 9/0031* (2013.01); *A61K 9/08* (2013.01); *A61K 31/196* (2013.01); *A61K 31/352* (2013.01); *A61K 31/353* (2013.01); *A61K 47/12* (2013.01)

(58) Field of Classification Search
CPC ..... A61K 31/56; A61K 31/573; A61K 47/22; A61K 9/08
USPC .................................................. 514/169, 177
See application file for complete search history.

(56) References Cited

U.S. PATENT DOCUMENTS 8,809,308 B2 * 8/2014 Palepu et al. ................. 514/169

* cited by examiner

*Primary Examiner* — Kevin E Weddington
(74) *Attorney, Agent, or Firm* — Lucas & Mercanti LLP

(57) ABSTRACT

Long term storage stable budesonide-containing solutions are disclosed. The solutions can include budesonide or a pharmaceutically acceptable salt thereof, cromolyn sodium, antioxidizing agent, benzoic acid, and a pharmaceutically acceptable fluid including propylene glycol and water. Kits including the long term storage stable budesonide-containing solutions and methods of treating ulcerative colitis are also disclosed.

21 Claims, No Drawings

ENEMA COMPOSITION FOR TREATMENT OF ULCERATIVE COLITIS HAVING LONG TERM STABILITY

CROSS-REFERENCE TO RELATED APPLICATION

This patent application is a continuation of U.S. patent application Ser. No. 14/076,566 filed Nov. 11, 2013, which in turn claims the benefit of priority under 35 U.S.C. §119(e) to U.S. Provisional Patent Application No. 61/724,678, filed Nov. 9, 2012, the contents of each of which are incorporated herein by reference.

BACKGROUND OF THE INVENTION

Ulcerative colitis (UC) is an inflammatory bowel disease characterized by recurrent bouts of rectal bleeding and bloody diarrhea. The initial inflammatory reaction begins in the rectal mucosa in over 95% of cases and may extend in a contiguous fashion to involve the whole colon. Treatment often involves administration of enemas containing corticosteroids, mesalamine and other ingredients which are useful in the largely palliative care and management of the disease. See, for example, Pravda's U.S. Pat. No. 7,312,243 and US Patent Application Publication No. 2010/0184728, the contents of each of which are incorporated herein by reference.

Multi-component enema products must often be compounded by a pharmacist upon need. Budesonide in a multi-component enema product is prone to oxidation and is, therefore, not suitable for long-term storage in a multi-component enema product. While multi-component enema products have shown promise in advancing therapies for patients with UC, there is an on-going need to provide the therapies in a form which would not only have improved shelf life but also in a format which would enhance patient compliance. The present invention addresses this need.

SUMMARY OF THE INVENTION

In some aspects of the invention, the budesonide-containing solutions include cromolyn sodium, an antioxidizing agent, benzoic acid and a pharmaceutically acceptable fluid including propylene glycol and water. The amount of budesonide included in the compositions is preferably from about 0.1 mg to about 10 mg and the amount of cromolyn sodium included in the compositions is preferably from about 5 mg to about 150 mg. Further aspects of the invention include kits containing a container including the budesonide-containing solutions and one or more separate containers including mesalamine, sodium butyrate, and lipoic acid. Still further aspects of the invention include methods of treatment using the kits.

One of the advantages of the inventive budesonide-containing solutions is that they have substantially improved long term stability. For example, the inventive solutions are substantially free of impurities, i.e. less than 5% total degradants, after about 3 months at a temperature of about 40° C.

DETAILED DESCRIPTION OF THE INVENTION

Unless defined otherwise, all technical and scientific terms used herein have the same meaning as is commonly understood by one of ordinary skill in the art to which this invention belongs. In the event that there is a plurality of definitions for a term herein, those in this section prevail unless stated otherwise.

As used herein, RRT is calculated by dividing the retention time of the peak of interest by the retention time of the main peak. Any peak with an RRT<1 elutes before the main peak, and any peak with an RRT>1 elutes after the main peak.

For purposes of the present invention, "substantially free of impurities" shall be understood to include budesonide-containing solutions in which the amount of total impurities is less than about 5%, as calculated on a normalized peak area response ("PAR") basis as determined by high performance liquid chromatography ("HPLC") at a wavelength of 223 nm, after a period of about 3 months at a temperature of 40° C. The amount of impurities is further calculated as being based upon the original amount budesonide being present in the solutions.

For purposes of the present invention, a pharmaceutically acceptable fluid is a fluid which is suitable for pharmaceutical use.

In one aspect of the invention, there are provided long-term stable budesonide-containing solutions including:
a) budesonide or a pharmaceutically acceptable salt thereof;
b) a stabilizing amount of cromolyn or a pharmaceutically acceptable salt or solvate thereof;
c) an antioxidizing agent;
d) a pharmaceutically acceptable organic acid; and
e) a pharmaceutically acceptable fluid including:
  i) propylene glycol; and
  ii) water.

The total degradants in the inventive solutions resulting from the degradation of the budesonide in the compositions is less than about 5% PAR as determined by HPLC at a wavelength of 223 nm after at least about 3 months at a temperature of about 40° C. The 40° C. stability translates into budesonide stability of at least 18 to 30 months under ambient storage conditions. Preferably, the budesonide-containing solutions demonstrate long term storage stability for at least about 2 years, especially when stored at the lower (refrigerated) temperatures. The inventive solutions exhibit less than half total degradants under refrigerated conditions compared to solutions that do not include cromolyn sodium.

In some aspects of the invention, the amount of budesonide in the inventive solutions is from about 0.1 mg to about 10 mg, preferably from about 2.5 mg to about 7.5 mg. It will be understood that solutions containing any useful concentration within the ranges, i.e. 0.5, 1, 2, 3, 4, 5, 6 . . . 10 are contemplated. Preferably, the budesonide amount is about 5 mg. In alternative aspects, the amount of budesonide is outside these ranges, but the amounts will be sufficient for single or multiple administrations of dosages generally regarded as effective amounts. In some aspects of the invention, pharmaceutically acceptable salts of budesonide are also contemplated.

In some aspects of the invention, the cromolyn is cromolyn sodium or cromolyn disodium.

Without meaning to be bound by any theory or hypothesis, the cromolyn sodium can have a stabilizing effect on the budesonide. For purposes of the present invention, "stabilizing amount" shall be understood to include those amounts which increase or enhance the stability of the budesonide in the compositions described herein. The stabilizing amount of cromolyn sodium stabilizes budesonide while also being effective at treating ulcerative colitis. In some aspects of the invention, a stabilizing amount of cromolyn sodium in the budesonide-containing solutions is from about 5 mg to about 150 mg, preferably from about 20 mg to about 125 mg. In other embodiments, the amount of cromolyn sodium is about 33 mg. In other embodiments, the amount of cromolyn sodium is about 70 mg. Preferably, the amount of cromolyn sodium is about 100 mg. In some aspects of the invention, the inventive compositions are substantially free of impurities, i.e. less than 5% total degradants after about 3 months at 40° C. Without meaning to be bound by any theory or hypothesis, less than 5% total degradants for budesonide shall be understood to be a level sufficient to maintain the therapeutic efficacy of budesonide.

The budesonide-containing solutions according to the invention may also include an antioxidizing agent that is pharmaceutically acceptable. For example, the antioxidizing agent can be selected from among bisulfites and their salts, sulfurous acid and salts, ascorbic/iso-ascorbic acid and their salts, thiols and mixtures thereof. Preferably, the antioxidizing agent is potassium metabisulfite. Suitable antioxidizing agent amounts in the inventive solutions can range from about 0.2 mg to about 20 mg, preferably from about 5 mg to about 15 mg. Preferably, the amount of the antioxidizing agent is about 10 mg.

In some aspects of the invention, the budesonide-containing solutions include a pharmaceutically acceptable organic acid, such as benzoic acid, citric acid, lactic acid, sorbic acid and mixtures thereof. Preferably, the organic acid is benzoic acid. The amount of the organic acid in the inventive solutions can be from about 0.2 mg to about 50 mg, and preferably from about 5 mg to about 15 mg, or from about 10 mg to about 20 mg. In some other embodiments, the amount of the organic acid in the budesonide-containing solutions is about 10 mg.

In several aspects of the invention, the pharmaceutically acceptable fluid includes a mixture of propylene glycol (PG) and water. For example, the pharmaceutically acceptable fluid can include about 50% PG and about 50% water. Alternatively, pharmaceutically acceptable fluid includes about 30% PG and about 70% water. The amount of PG and water can also be varied within the ranges, i.e. the ratio of PG:water in the pharmaceutically acceptable fluid can range from about 75:25 to about 30:70. Within this range, is a pharmaceutically acceptable fluid containing about 75% PG and about 25% water, and preferably 50% PG and 50% water.

Further embodiments of the invention include long-term stable budesonide-containing solutions such as those described above and further having the characteristics of

| Ingredient | % by Weight Range | Range per unit dose |
|---|---|---|
| budesonide | about 0.001 to about 0.1 | 0.1 to 10 mg |
| cromolyn sodium | about 0.05 to about 0.2 | 5 to 1000 mg |
| antioxidizing agent | about 0.002 to about 0.2 | 0.2 to 20 mg |
| organic acid | about 0.002 to about 0.2 | 0.2 to 50 mg |
| propylene glycol | about 10 to about 90 | 1 g to 9 g |
| water | about 10 to about 90 | 1 g to 9 g |
| auxiliary ingredients/excipients | 0 to about 10% | 0 to 1 g |
| total | 100 | 10 g |

Other additives which may be included in the solutions include free radical or metal scavengers such as EDTA and lactobionic acid.

In some aspects of the invention, the amounts of the ingredients of the inventive solutions are provided per unit dose. Preferably, the unit dose volume is from about 5 ml to about 15 ml. In some aspects the unit dose volume is from about 10 ml to about 15 ml. In alternative aspects, the volume is outside these ranges, but the amounts of the ingredients will be sufficient for single or multiple administrations of dosages. Preferably, the unit dose volume is about 10 ml.

The budesonide-containing solutions described herein have advantageously long term stability. For example, the inventive solutions have less than 0.2% total (budesonide) degradants after 3 months at 5° C. The amount of total degradants in the solution after 3 months at 25° C. is less than 0.5%. While the amount of total degradants in the solution after 3 months at 40° C. is less than 5%. These accelerated stability data confirm that the shelf life of the solutions is well in excess of one year or longer when stored at room temperature or when refrigerated.

The invention also includes kits for the treatment of ulcerative colitis. Some preferred kits in accordance with the invention include a plurality of containers suitable for holding pharmaceutically acceptable materials. A first container includes a therapeutically effective amount of the long-term stable budesonide-containing solutions described herein. A second container includes a therapeutically effective amount of mesalamine or pharmaceutically acceptable aminosalicylic acid. In some aspects, the mesalamine is kept at a pH of below about 5.0. In some aspects of the invention, the second container optionally includes sodium butyrate. In other aspects of the invention, the kit includes a third container that includes a therapeutically sufficient amount of sodium butyrate.

According to several preferred aspects of the invention, the container contents are formulated for rectal administration. In some aspects of the invention, the container contents are in a suppository form or an enema solution. Preferably the contents are an enema product. The contents of the containers found in the kit are combined using techniques well known to those of ordinary skill in order to form a product for rectal administration which is ready for administration to a patient in need thereof.

In some preferred aspects of the invention the second vessel includes mesalamine or a pharmaceutically acceptable salt thereof, as well as pharmaceutically acceptable agents including an acidifying agent, an antioxidizing agent, an antimicrobial preservative, free radical scavengers or metal scavengers, a mixture of microcrystalline cellulose (MCC) and carboxymethylcellulose (CMC), and water. In other aspects of the invention, the second vessel also includes sodium butyrate.

The amount of mesalamine or a pharmaceutically acceptable salt thereof typically included in unit doses included in the kits is from about 50 mg to about 5,000 mg, preferably from about 750 mg to about 3000 mg or from about 1500 mg to about 2600 mg. Preferably, the amount of mesalamine or a pharmaceutically acceptable salt thereof included in unit doses included in the second vessel is about 2000 mg.

The acidifying agent can be selected from acetic acid, citric acid, scorbic acid, lactic acid, HCl and phosphoric acid. Preferably, the acidifying agent is citric acid. The amount of the acidifying agent included in unit doses in the kits is from about 75 mg to about 150 mg, and preferably 100 mg.

The antioxidizing agent in the second vessel in the kits can be selected from among bisulfites and their salts, sulfurous acid and salts, ascorbic/iso-ascorbic acid and their salts, thiols and mixtures thereof. Preferably, the antioxidizing agent is potassium metabisulfite. The amount of the antioxidizing agent included in unit doses in the second vessel is from about 40 mg to about 80 mg, and preferably about 60 mg.

The antimicrobial preservative can be selected from benzoic acid and salts, sorbic acid and salts, boric acids and salts, parabens, imidurea, monothioglycerol, pentetic acid, phenyl mercuric borate, phenyl mercuric nitrate, potassium metabisulfite, propionic acid, lactic acids and salts, sodium sulfite, and thimerosol. Preferably, the antimicrobial preservative is sodium benzoate. The amount of the antimicrobial preservative included in unit doses in the kits is from about 150 mg to about 250 mg, and preferably about 180 mg.

The metal scavenger in the second vessel in the kits can be selected from among EDTA and lactobionic acid. Preferably, the metal scavenger is EDTA. The amount of metal scavenger included in unit doses in the second vessel is from about 40 mg to about 70 mg, and preferably about 50 mg.

Some embodiments also include an effective amount of a chain stopper (i.e., a free radical scavenger). Free radical scavengers are selected from BHT, BHA, alpha-tocopherol and its various pharmaceutical forms, propyl gallate and other compounds that are known to scavenge free radicals. The amount of the free radial scavenger is determined by the nature of each compound. For example, BHT and BHA are present in quantities of from about 0.0005% to about 0.3% within the formulation. Alpha-tocopherol are present in quantities of from about 0.001% to 0.05% within the formulation.

The mixture of MCC and CMC in the kits according to several aspects of the invention can be mixtures of MCC and CMC such as the products available under the trade name of AVICEL, i.e. AVICEL RC-591 and AVICEL CL-611. Preferably, the mixture of MCC and CMC is a blend of microcrystalline cellulose and sodium carboxymethylcellulose, such as AVICEL RC-591. The amount of the mixture of MCC and CMC included in unit doses in the kits is from about 500 mg to about 1.5 g, and preferably from about 590 mg to about 1 g. Preferably, the amount of mixture of MCC and CMC is about 590 mg.

The amount of sodium butyrate typically included in unit doses in the kits is from about 5 millimoles to about 50 millimoles, preferably 15 millimoles. In other aspects of the invention, the amount of sodium butyrate is from about 0.56 mg to about 5.55 g, preferably 100 mg to 1700 mg. In some embodiments, the amount is 125 mg. In other embodiments, the amount is 1,665 mg.

In some aspects of the invention, the amounts of the ingredients of the solutions in the second container are provided per unit dose. Preferably, the unit dose volume in the second container is from about 40 ml to about 70 ml. In some aspects the unit dose volume in the second container is from about 50 ml to about 60 ml. In alternative aspects, the volume in the second container is outside these ranges, but the amounts will be sufficient for single or multiple administrations of dosages. Preferably, the unit dose volume in the second container is about 60 ml.

In some aspects of the invention, the amounts of the ingredients of the contents of the third container are provided per unit dose. Preferably, the unit dose volume in the third container is from about 5 ml to about 15 ml. In some aspects the unit dose volume in the third container is about 10 ml. In some aspects of the invention, the contents of the third container are formulated as an enema product. In alternative aspects, the contents of the third container include a suppository. Preferably, the contents of the third container are formulated as an enema product.

In some aspects of the invention, sodium butyrate can be formulated as a separate entity. The sodium butyrate can be formulated as a suppository or an aqueous enema solution. In some embodiments, after rectal administration of an enema product as described herein, a sodium butyrate suppository can be inserted to prevent any leakage of enema. Preferably, the suppository will dissolve in 30 to 45 minutes. In alternative embodiments, an aqueous enema solution of sodium butyrate (1.6 g in 10 ml water) can be added to the combined contents of the first and second containers.

In some aspects of the invention, the kit may also optionally include an effective amount of a lipoic acid provided in a separate container. The lipoic acid is selected from alpha lipoic acid and R-dihydro-lipoic acid. Preferably, the lipoic acid is R-dihydro-lipoic acid. The amount of lipoic acid is provided per unit dose. Preferably, the amount of lipoic acid is from about 100 mg to about 1,000 mg, preferably from about 250 mg to about 750 mg. In some aspects, the amount of lipoic acid is outside these ranges, but the amounts will be sufficient for single or multiple administrations of dosages. Preferably the amount of lipoic acid is 300 mg. The lipoic acid is preferably formulated for oral administration. The contents of the container including lipoic acid found in the kit are prepared using techniques well known to those of ordinary skill in order to form a product for oral administration which is ready for administration to a patient in need thereof.

As will be appreciated by those of ordinary skill, the kits will contain other pharmaceutically necessary materials for storing and/or administering the drug, including instructions for storage and use, additional diluents, if desired, etc.

Another embodiment of the invention provides methods of treating ulcerative colitis. The methods include administering to a patient in need thereof the contents of one of the kits containing the budesonide-containing solutions described herein. The methods include providing to a patient in need thereof one of the kits described herein, subsequently combining the contents of the first, second, and, if present, third containers to form an enema composition, and rectally administering the resulting combination, optionally in combination with oral administration of lipoic acid.

EXAMPLES

Following are examples which illustrate procedures for practicing the invention. These examples should not be construed as limiting. All percentages are by weight and all solvent mixture proportions are by volume unless otherwise noted.

Example 1

Budesonide-containing bulk solutions were prepared as follows:

Formulation A (Comparative) was prepared by combining 75.8 mg of budesonide, 150.2 mg of benzoic acid, and 150.3 mg potassium metabisulfite and mixed. 75 ml of propylene glycol was added and then 75 ml of water for injection was added to the budesonide, benzoic acid and potassium metabisulfite mixture. The mixture was then sonicated for 5-6 minutes to obtain a clear solution. The budesonide-containing solution was then transferred to bottles and capped, with each bottle containing 10 ml. The samples were maintained at 40° C./75% relative humidity (RH), and 25° C./60% RH and 5° C./60% RH and analyzed after 15 days, one month, three months or five months for drug content and impurity profile as indicated in Table 1. The results obtained are presented in Table 1.

Formulation B (Inventive) was prepared by combining 75.7 mg of budesonide, 521.1 mg of cromolyn sodium, 150 mg of benzoic acid, and 150.5 mg potassium metabisulfite and mixed. 75 ml of propylene glycol was added and then 75 ml of water for injection was added to the budesonide, cromolyn sodium, benzoic acid and potassium metabisulfite mixture. The mixture was then sonicated for 5-6 minutes to obtain a clear solution. The budesonide-containing solution was then transferred to bottles and capped, with each bottle containing 10 ml. The samples were maintained at 40°

C./75% RH, and 25° C./60% RH and 5° C./60% RH and analyzed after 15 days, one month, three months or five months for drug content and impurity profile as indicated in Table 1. The results obtained are presented in Table 1.

Formulation C (Inventive) was prepared by combining 75.71 mg of budesonide, 1.1 g of cromolyn sodium, 150 mg of benzoic acid, and 150.2 mg potassium metabisulfite and mixed. 75 ml of propylene glycol was added and then 75 ml of water for injection was added to the budesonide, cromolyn sodium, benzoic acid and potassium metabisulfite mixture. The mixture was then sonicated for 5-6 minutes to obtain a clear solution. The budesonide-containing solution was then transferred to bottles and capped, with each bottle containing 10 ml. The samples were maintained at 40° C./75% RH, and 25° C./60% RH and 5° C./60% RH and analyzed after 15 days, one month, three months or five months for drug content and impurity profile as indicated in Table 1. The results obtained are presented in Table 1.

Formulation D (Inventive) was prepared by combining 75.73 mg of budesonide, 1.578 g of cromolyn sodium, 150.1 mg of benzoic acid, and 150 mg potassium metabisulfite and mixed. 75 ml of propylene glycol was added and then 75 ml of water for injection was added to the budesonide, cromolyn sodium, benzoic acid and potassium metabisulfite mixture. The mixture was then sonicated for 5-6 minutes to obtain a clear solution. The budesonide-containing solution was then transferred to bottles and capped, with each bottle containing 10 ml. The samples were maintained at 40° C./75% RH, and 25° C./60% RH and 5° C./60% RH and analyzed after 15 days, one month, or three months for budesonide content and impurity profile as indicated in Table 1 and cromolyn sodium content as indicated in Table 2. The results obtained are presented in Table 1 and Table 2.

TABLE 1

Stability of Budesonide

| Formulation | Temp | Time period | Content (mg/mL) | % of Initial | % total degradants | Remarks |
|---|---|---|---|---|---|---|
| Formulation A (Comparative) | | | | | | |
| Budesonide-5 mg | Initial | 0 | 0.51 | 100.0 | 0.00 | Clear colorless solution |
| Benzoic acid-10 mg | 40° C. | 15 D | 0.48 | 94.1 | 3.02 | Clear colorless solution |
| Potassium | | 1 M | 0.45 | 88.2 | 7.54 | Clear colorless solution |
| metabisulfite-10 mg | | 3 M | 0.24 | 47.1 | 14.8 | Clear colorless solution |
| Propylene glycol-5 mL | 25° C. | 15 D | 0.50 | 98.0 | 1.81 | Clear colorless solution |
| WFI qs 5 mL | | 1 M | 0.48 | 94.1 | 2.30 | Clear colorless solution |
| | | 3 M | 0.46 | 90.2 | 3.95 | Clear colorless solution |
| | 5° C. | 15 D | 0.52 | 102.0 | 0.28 | Clear colorless solution |
| | | 1 M | 0.52 | 102.0 | 0.40 | Clear colorless solution |
| | | 3 M | 0.52 | 102.0 | 0.45 | Clear colorless solution |
| Formulation B | | | | | | |
| Budesonide-5 mg | Initial | 0 | 0.53 | 100.0 | Not detected | Clear colorless solution |
| Cromolyn sodium-33 mg | | | | | | |
| Benzoic acid-10 mg | 40° C. | 15 D | 0.52 | 98.1 | 0.15 | Clear colorless solution |
| Potassium | | 1 M | 0.52 | 98.1 | 0.06 | Clear colorless solution |
| metabisulfite-10 mg | | 3 M | 0.52 | 98.1 | 0.06 | Clear colorless solution |
| Propylene glycol-5 mL | 25° C. | 15 D | 0.52 | 98.1 | 0.15 | Clear colorless solution |
| WFI qs 5 mL | 5° C. | 15 D | 0.52 | 98.1 | 0.15 | Clear colorless solution |
| Formulation C | | | | | | |
| Budesonide-5 mg | Initial | 0 | 0.51 | 100.0 | Not detected | Clear colorless solution |
| Cromolyn sodium-66 mg | | | | | | |
| Benzoic acid-10 mg | 40° C. | 15 D | 0.51 | 100.0 | 0.14 | Clear colorless solution |
| Potassium | | 1 M | 0.50 | 98.0 | 0.27 | Clear colorless solution |
| metabisulfite-10 mg | | 3 M | 0.51 | 100 | 0.08 | Clear colorless solution |
| Propylene glycol-5 mL | 25° C. | 15 D | 0.51 | 100.0 | 0.00 | Clear colorless solution |
| WFI qs 5 mL | 5° C. | 15 D | 0.51 | 100.0 | 0.00 | Clear colorless solution |
| Formulation D | | | | | | |
| Budesonide-5 mg | Initial | 0 | 0.50 | 100 | Not detected | Clear colorless solution |
| Cromolyn sodium-100 mg | | | | | | |
| Benzoic acid-10 mg | 40° C. | 15 D | 0.50 | 100 | 0.10 | Clear colorless solution |
| Potassium | | 1 M | 0.50 | 100 | 0.43 | Clear colorless solution |
| metabisulfite-10 mg | | 3 M | 0.48 | 96.0 | 3.87 | Clear colorless solution |
| Propylene glycol-5 mL | 25° C. | 15 D | 0.50 | 100 | 0.00 | Clear colorless solution |
| WFI qs 5 mL | 5° C. | 15 D | 0.50 | 100 | 0.00 | Clear colorless solution |

TABLE 2

Stability of Cromolyn Sodium

| Formulation | Temp | Time period | Content (mg/mL) | % of Initial |
|---|---|---|---|---|
| Formulation B | | | | |
| Budesonide-5 mg | Initial | 0 | 3.27 | 100 |
| Cromolyn sodium-33 mg | 40° C. | 15 D | 3.25 | 99.4 |
| Benzoic acid-10 mg | | 1 M | 3.27 | 100 |
| | | 3 M | 3.29 | 100.6 |
| Potassium metabisulfite-10 mg | 25° C. | 15 D | 3.22 | 98.5 |
| Propylene glycol-5 mL | 5° C. | 15 D | 3.31 | 101.2 |
| WFI qs 5 mL | | | | |
| Formulation C | | | | |

TABLE 2-continued

Stability of Cromolyn Sodium

| Formulation | Temp | Time period | Content (mg/mL) | % of Initial |
|---|---|---|---|---|
| Budesonide-5 mg | Initial | 0 | 6.46 | 100.0 |
| Cromolyn sodium-66 mg | 40° C. | 15 D | 6.19 | 95.8 |
| | | 1 M | 6.34 | 98.1 |
| Benzoic acid-10 mg | | 3 M | 6.34 | 98.1 |
| | 25° C. | 15 D | 6.37 | 98.6 |
| Potassium metabisulfite-10 mg | 5° C. | 15 D | 6.46 | 100.0 |
| Propylene glycol-5 mL | | | | |
| WFI qs 5 mL | | | | |
| Formulation D | | | | |
| Budesonide-5 mg | Initial | 0 | 9.7 | 100 |
| Cromolyn sodium-100 mg | 40° C. | 15 D | 9.52 | 98.1 |
| | | 1 M | 9.80 | 101.0 |
| Benzoic acid-10 mg | | 3 M | 9.67 | 99.7 |
| | 25° C. | 15 D | 9.63 | 99.3 |
| Potassium metabisulfite-10 mg | 5° C. | 15 D | 9.88 | 101.9 |
| Propylene glycol-5 mL | | | | |
| WFI qs 5 mL | | | | |

As shown in Table 1, the inventive budesonide-containing solutions are very stable in solutions containing cromolyn sodium. Table 1 shows that solutions containing budesonide in the presence of from 5 mg to 150 mg cromolyn sodium, had less than about 5% total degradants due to the degradation of budesonide after 3 months storage at 40° C. Even at refrigerated conditions, i.e. 5° C., the inventive solutions demonstrate a 50% or better improvement over the comparative sample. The data presented in Table 2 shows that cromolyn sodium is also stable after 3 months storage at 40° C.

The data presented in Tables 1 and 2 translates to budesonide-containing solutions including 5 mg to 150 mg cromolyn sodium having a shelf life of at least about 18 months at ambient storage conditions. In fact, the inventive compositions are expected to be stable for at least 30 months under ambient storage conditions with much lower degradation than the comparative sample. In contrast, the sample which did not contain cromolyn sodium exhibited more than 14% total degradants under the same storage conditions. Such solutions would not be suitable for long-term storage as described herein.

Example 2

Formulation E (Inventive) was prepared in the same manner as Formulation D in Example 1 above. The samples were maintained at 25° C./60% RH and 5° C./60% RH and analyzed after 15 days, one month, or three months for budesonide content and impurity profile as indicated in Table 3. The results obtained are presented in Table 3.

TABLE 3

Stability of Budesonide

| Formulation E | Temp | Time period | Content (mg/mL) Budesonide | % of Initial | % of total degradants |
|---|---|---|---|---|---|
| Budesonide-5 mg | Initial | | 0.52 | 100.0 | |
| Cromolyn sodium-100 mg | 25° C. | 15 D | 0.53 | 101.5 | |
| | | 1 M | 0.53 | 101.9 | |
| Benzoic Acid-10 mg | | 3 M | 0.53 | 101.9 | 0.31 |
| Potassium metabisulfite-10 mg | 5° C. | 15 D | 0.53 | 101.7 | |
| | | 1 M | 0.53 | 101.9 | |
| Propylene glycol-5 mL | | 3 M | 0.53 | 101.9 | 0.00 |
| WFI - 5 mL | | | | | |

As shown in the table, less than about 0.5% potency loss of budesonide was observed when stored at 25° C. for 3 months. These data suggest that solutions containing budesonide in the presence of from 5 mg to 150 mg cromolyn sodium are stable for at least 18 to 30 months under ambient storage conditions. Disodium cromolyn is not a recognized stabilizing agent. However, it was found that the improved stability of budesonide in the presence of disodium cromolyn is unexpected.

Example 3

Mesalamine-containing bulk compositions were prepared as follows:

Formulation F (Inventive) was prepared by adding 2.61 g sodium benzoate to 500 ml water for injection and mixing for about 5 minutes. 0.84 g potassium metabisulfite was added to the sodium benzoate composition and mixed for about 5 minutes. 14.5 g of AVICEL RC-591 was added to the sodium benzoate and potassium metabisulfite composition and mixed for about 15 minutes. 29.89 g of mesalamine was added to the sodium benzoate, potassium metabisulfite, and AVICEL RC-591 composition. The composition was mixed for about 15 minutes and the pH of the mixture was 5.25. 1.45 g of citric acid was then added to the composition and mixed for about 5 minutes. 0.725 g of EDTA was added, and the resultant composition was mixed from about 5 minutes. The pH of the composition was 4.25. Subsequently, 1.83 g of sodium butyrate was added to the composition and mixed for about 20 minutes. The pH of the composition was 4.45. The resultant composition was then transferred to 40 cc bottles and sealed, with each bottle containing 10 ml. The samples were maintained at 40° C./75% RH, and 25° C./60% RH and 5° C./60% RH and analyzed after 15 days, one month, three months or five months for drug content and impurity profile as indicated in Table 4. The results obtained are presented in Table 4.

Formulation G (Inventive) was prepared by adding 2.61 g sodium benzoate to 500 ml water for injection and mixing for about 5 minutes. 840.3 mg potassium metabisulfite was added to the sodium benzoate composition and mixed for about 5 minutes. 14.45 g of AVICEL RC-591 was added to the sodium benzoate and potassium metabisulfite composition and mixed for about 30 minutes. 29.94 g of mesalamine was added to the sodium benzoate, potassium metabisulfite, and AVICEL RC-591 composition. The composition was mixed for about 15 minutes and the pH of the mixture was 5.24. 1.44 g of citric acid was then added to the composition and mixed for about 5 minutes. 720.5 mg of EDTA was added, and the resultant composition was mixed from about 5 minutes. The pH of the composition was 4.24. Subsequently, 1.83 g of sodium butyrate was added to the composition and mixed for about 20 minutes. The pH of the composition was 4.50. The resultant composition was then transferred to 40 cc bottles and sealed, with each bottle containing 10 ml. The samples were maintained at 40° C./75% RH, and 25° C./60% RH and 5° C./60% RH and analyzed after 7 days, 14 days, one month or three months for drug content and impurity profile as indicated in Table 4. The results obtained are presented in Table 4.

TABLE 4

Stability of Mesalamine and Sodium Butyrate

| | Temp | Time period | Content (mg/mL) | % of Initial | % total degradants |
|---|---|---|---|---|---|
| Formulation F | | Mesalamine | | | |
| Mesalamine-2.08 g | Initial | | 41.1 | 100 | 0.00 |
| Sodium butyrate-125 mg | 40° C. | 7 D | 28.4 | 69.2 | 0.21 |
| | | 14 D | 57.5 | 140.1 | 0.14 |
| Citric acid anydrous-100 mg | 25° C. | 7 D | 27.0 | 65.8 | 0.07 |
| | | 14 D | 70.9 | 172.7 | 0.00 |
| Potassium metabi- | | Sodium Butyrate | | | |
| sulfite-58.3 mg | Initial | | 2.58 | 100 | Not detected |
| Sodium benzoate-180 mg | 40° C. | 7 D | 2.56 | 99.2 | |
| | 25° C. | 7 D | 2.56 | 99.2 | |
| EDTA-50 mg | | | | | |
| AVICEL RC 591-1 g | | | | | |
| WFI qs 50 mL | | | | | |
| Formulation G | | Mesalamine | | | |
| Mesalamine-2.08 g | Initial | | 41.8 | 100 | 0.00 |
| Sodium butyrate-125 mg | 40° C. | 1 M | 41.6 | 99.5 | 0.21 |
| | | 2 M | 41.5 | 99.3 | 0.27 |
| Citric acid anydrous-100 mg | | 3 M | 41.4 | 99.0 | 0.96 |
| Potassium metabi- | | Sodium Butyrate | | | |
| sulfite-58.3 mg | Initial | | 2.49 | 100 | Not detected |
| Sodium benzoate-180 mg | 40° C. | 1 M | 2.49 | 100 | |
| | | 2 M | 2.49 | 100 | |
| EDTA-50 mg | | 3 M | 2.45 | 98.4 | |
| AVICEL RC 591-1 g | | | | | |
| WFI qs 50 mL | | | | | |

As shown in Table 4, the compositions containing mesalamine and sodium butyrate are very stable. Table 4 shows that compositions containing mesalamine and sodium butyrate had less than about 1% total degradants due to the degradation of mesalamine after 3 months storage at 40° C. The data presented in Table 4 also shows that cromolyn sodium is stable after 3 months storage at 40° C. The data presented in Table 4 translates to compositions containing mesalamine and sodium butyrate having a shelf life of at least about 18 months at ambient storage conditions.

What is claimed is:

1. A long-term stable budesonide-containing solution, comprising
   a) budesonide or a pharmaceutically acceptable salt thereof;
   b) cromolyn or a pharmaceutically acceptable salt or solvate thereof;
   c) an antioxidizing agent;
   d) benzoic acid; and
   e) a pharmaceutically acceptable fluid comprising propylene glycol and water.

2. The long-term stable budesonide-containing solution of claim 1, wherein the amount of the budesonide is from about 0.1 mg to about 1.0 mg.

3. The long-term stable budesonide-containing solution of claim 1, wherein the cromolyn is cromolyn sodium, present in an amount of from about 5 mg to about 150 mg.

4. The long-term stable budesonide-containing solution of claim 1, wherein the antioxidizing agent is selected from the group consisting of potassium metabisulfite, sodium metabisulfite, sulfurous acid, ascorbic/iso-ascorbic acid and their salts, thiols and mixtures thereof.

5. The long-term stable budesonide-containing solution of claim 4, wherein the antioxidizing agent is potassium metabisulfite.

6. The long-term stable budesonide-containing solution of claim 1, wherein the amount of the antioxidizing agent is from about 0.2 mg to about 20 mg.

7. The long-term stable budesonide-containing solution of claim 1, wherein the amount of benzoic acid is from about 5 mg to about 50 mg.

8. The long-term stable budesonide-containing solution of claim 1, wherein the pharmaceutically acceptable fluid comprises from about 20% (v/v) to about 90% (v/v) propylene glycol.

9. The long-term stable budesonide-containing solution of claim 8, wherein the pharmaceutically acceptable fluid comprises about 50% (v/v) propylene glycol.

10. The long-term stable budesonide-containing solution of claim 1, further comprising a free radical scavenger or metal scavenger.

11. The long-term stable budesonide-containing solution of claim 10, wherein the metal scavenger is selected from the group consisting of EDTA and lactobionic acid.

12. The long-term stable budesonide-containing solution of claim 1, wherein the total volume of the solution is from about 5 ml to about 15 ml.

13. A long-term stable budesonide-containing solution of claim 1, wherein the amount of total degradants in the solution after 3 months at 40° C. is less than 5%.

14. A kit for the treatment of ulcerative colitis, comprising:
   a) a first container comprising a therapeutically effective of amount of the long-term stable budesonide-containing solution of claim 1; and
   b) a second container comprising:
      i) from about 50 mg to about 5,000 mg mesalamine or a pharmaceutically acceptable salt thereof;
      ii) from about 5 millimoles to about 50 millimoles sodium butyrate;
      iii) from about 75 mg to about 150 mg citric acid;
      iv) from about 40 mg to about 80 mg potassium metabisulfite;
      v) from about 150 mg to about 250 mg sodium benzoate;
      vi) from about 40 mg to about 70 mg EDTA;
      vii) from about 500 mg to about 1.5 g of a mixture of microcrystalline cellulose and carboxymethylcellulose; and
      viii) water.

15. A kit for the treatment of ulcerative colitis, comprising:
   a) a first container comprising a therapeutically effective of amount of the long-term stable budesonide-containing solution of claim 1;
   b) a second container comprising:
      i) from about 50 mg to about 5,000 mg mesalamine or a pharmaceutically acceptable salt thereof;
      ii) from about 5 millimoles to about 50 millimoles sodium butyrate;
      iii) from about 75 mg to about 150 mg citric acid;
      iv) from about 40 mg to about 80 mg potassium metabisulfite;
      v) from about 150 mg to about 250 mg sodium benzoate;
      vi) from about 40 mg to about 70 mg EDTA;

vii) from about 500 mg to about 1.5 g of a mixture of microcrystalline cellulose and carboxymethylcellulose; and
viii) water; and
c) a third container comprising from about 100 mg to about 1,000 mg lipoic acid.

16. A kit for the treatment of ulcerative colitis, comprising:
a) a first container comprising a therapeutically effective of amount of the long-term stable budesonide-containing solution of claim 1,
b) a second container comprising:
   i) from about 50 mg to about 5,000 mg mesalamine or a pharmaceutically acceptable salt thereof;
   ii) from about 75 mg to about 150 mg citric acid;
   iii) from about 40 mg to about 80 mg potassium metabisulfite;
   iv) from about 150 mg to about 250 mg sodium benzoate;
   v) from about 40 mg to about 70 mg EDTA;
   vi) from about 500 mg to about 1.5 g of a mixture of microcrystalline cellulose and carboxymethylcellulose; and
   vii) water; and
c) a third container comprising;
   i) from about 5 millimoles to about 50 millimoles sodium butyrate; and
   ii) water.

17. A kit for the treatment of ulcerative colitis, comprising:
a) a first container comprising a therapeutically effective of amount of the long-term stable budesonide-containing solution of claim 1,
b) a second container comprising:
   i) from about 50 mg to about 5,000 mg mesalamine or a pharmaceutically acceptable salt thereof;
   ii) from about 75 mg to about 150 mg citric acid;
   iii) from about 40 mg to about 80 mg potassium metabisulfite;
   iv) from about 150 mg to about 250 mg sodium benzoate;
   v) from about 40 mg to about 70 mg EDTA;
   vi) from about 500 mg to about 1.5 g of a mixture of microcrystalline cellulose and carboxymethylcellulose; and
   vii) water;
c) a third container comprising;
   i) from about 5 millimoles to about 50 millimoles sodium butyrate; and
   ii) water; and
d) a fourth container comprising from about 100 mg to about 1,000 mg lipoic acid.

18. A method of treating ulcerative colitis in a patient requiring such treatment, comprising:
a) providing the kit of claim 14;
b) combining the contents of the first and second containers; and
c) rectally administering the resulting combination of step b).

19. A method of treating ulcerative colitis in a patient requiring such treatment, comprising:
a) providing the kit of claim 15;
b) combining the contents of the first and second containers;
c) rectally administering the resulting combination of step b); and
d) orally administering the lipoic acid of the third container.

20. A method of treating ulcerative colitis in a patient requiring such treatment, comprising:
a) providing the kit of claim 16;
b) combining the contents of the first, second, and third containers;
c) rectally administering the resulting combination of step b).

21. A method of treating ulcerative colitis in a patient requiring such treatment, comprising:
a) providing the kit of claim 17;
b) combining the contents of the first, second, and third containers;
c) rectally administering the resulting combination of step b); and
d) orally administering the lipoic acid of the fourth container.

* * * * *